United States Patent
Connor et al.

(10) Patent No.: US 6,527,718 B1
(45) Date of Patent: Mar. 4, 2003

(54) ULTRASOUND SYSTEM FOR CONTINUOUS IMAGING AND DELIVERY OF AN ENCAPSULATED AGENT

(76) Inventors: Brian G Connor, 11 High Rock La., Newfields, NH (US) 03856; Matthew Mooney, 62 Buckboard Dr., Westford, MA (US) 01886

( * ) Notice: Subject to any disclaimer, the term of this patent is extended or adjusted under 35 U.S.C. 154(b) by 0 days.

(21) Appl. No.: 09/535,762

(22) Filed: Mar. 28, 2000

Related U.S. Application Data
(60) Provisional application No. 60/150,045, filed on Aug. 20, 1999.

(51) Int. Cl.[7] .................................................. A61B 8/00
(52) U.S. Cl. ....................................... 600/439; 600/458
(58) Field of Search ................................ 600/407, 420, 600/437, 431, 439, 427, 459, 449, 458, 466, 467; 424/9.52, 9.51, 9.5, 450

(56) References Cited

U.S. PATENT DOCUMENTS

| | | | | |
|---|---|---|---|---|
| 4,920,969 A | * | 5/1990 | Suzuki et al. | 600/436 |
| 5,007,427 A | * | 4/1991 | Suzuki et al. | 2/102 |
| 5,072,458 A | * | 12/1991 | Suzuki | 2/102 |
| 5,111,818 A | * | 5/1992 | Suzuki et al. | 600/390 |
| 5,190,766 A | * | 3/1993 | Ishihara | 424/489 |
| 5,255,683 A | | 10/1993 | Monaghan | 128/662.02 |
| 5,381,794 A | * | 1/1995 | Tei et al. | 600/459 |
| 5,456,257 A | | 10/1995 | Johnson et al. | 128/662.02 |
| 5,558,092 A | | 9/1996 | Unger et al. | 128/660.03 |
| 5,577,505 A | | 11/1996 | Brock-Fisher et al. | 128/662.02 |
| 5,598,845 A | * | 2/1997 | Chandraratna et al. | 600/459 |
| 5,675,554 A | | 10/1997 | Cole et al. | 367/138 |
| 5,706,819 A | | 1/1998 | Hwang et al. | 128/662.02 |
| 5,740,128 A | | 4/1998 | Hossack et al. | 367/138 |
| 5,833,613 A | | 11/1998 | Averkiou et al. | 600/440 |
| 6,039,967 A | | 3/2000 | Ottoboni et al. | 424/426 |
| 6,231,834 B1 | * | 5/2001 | Unger et al. | 600/431 |
| 6,242,472 B1 | * | 6/2001 | Sekins et al. | 514/396 |

FOREIGN PATENT DOCUMENTS

| | | |
|---|---|---|
| EP | 0851241 A2 | 7/1998 |
| WO | WO 96/22111 | 7/1996 |
| WO | WO 98/48783 | 11/1998 |
| WO | WO 99/39697 | 8/1999 |
| WO | WO 00/12062 | 3/2000 |

OTHER PUBLICATIONS

P. Rafter, "Harmonic Power Doppler Technology", 4th Heart Centre Sym. on Ultrasound Contrast Imaging, Jan. 21–22, 1999, 2 pages.

J. Cheirif, "HP Acoustic Densitometry: A New Echocardiographic Method for the On–Line Quantitative Assess ment of Contrast Echocardiograms", Application Note, 1996, 4 pages.

D. L. Miller, "Ultrasonic Detection of Resonant Cavitation Bubbles in a Flow Tube by their Second Harmonic Emissions", Ultrasonics, Sep. 1981, pp. 217–224.

\* cited by examiner

*Primary Examiner*—Marvin M. Lateef
*Assistant Examiner*—Ali M. Imam
(74) *Attorney, Agent, or Firm*—John Vodopia

(57) ABSTRACT

An ultrasound system for continuous imaging and for controlling release of an encapsulated agent from a carrier comprises a housing secured to a patient's body, a transducer mounted within the housing, means for controlling the transducer to insonify the drug carrier with an ultrasonic signal and to thereby cause the release of the agent, and means for processing an ultrasonic echo signal to produce an image. Also, a method for controlling release of an encapsulated agent from a carrier comprises the steps of measuring a physiological parameter of a patient based on an ultrasonic echo signal, comparing the physiological parameter to a threshold, and transmitting an ultrasonic signal to insonify the carrier and thereby cause the release of the agent from the carrier in accord with the measured physiological parameter.

20 Claims, 5 Drawing Sheets

SCANNED SECTOR

ULTRASOUND SYSTEM FOR CONTINUOUS IMAGING AND DELIVERY OF AN ENCAPSULATED AGENT

CROSS-REFERENCE TO RELATED APPLICATIONS

This patent application is a continuation-in-part of a co-pending provisional application entitled METHODS AND APPARATUS FOR DISPLAYING INFORMATION RELATING TO DELIVERY AND ACTIVATION OF A THERAPEUTIC AGENT USING ULTRASOUND ENERGY, Ser. No. 60/150,045, filed Aug. 20, 1999, incorporated herein by reference.

FIELD OF THE INVENTION

The present invention relates to ultrasound systems and, more particularly, to an ultrasound system for continuous imaging of an organ inside a patient's body and for controlling release of an encapsulated agent from a carrier.

BACKGROUND OF THE INVENTION

Ultrasound technology is widely used for imaging various organs in a patient's body and for diagnosis of tissue pathology. Commonly, ultrasound examinations are performed by placing a probe containing an ultrasound transducer on the surface of the patient's body. This is done to make a specific diagnosis and not for prolonged monitoring of the patient.

U.S. Pat. No. 5,598,845 to Chandraratna et al. (hereinafter "the '845 patent"), entitled Ultrasound Transducer Device For Continuous Imaging Of The Heart And Other Body Parts, which is incorporated herein by reference, describes an ultrasound transducer device that can be used for continuous imaging of a patient's heart or other body organs for diagnosis or monitoring. An ultrasound transducer is mounted in an enclosure that is secured to a holding pad, and the holding pad is attached to a surface of a patient's body. The significant features of two embodiments of such a device are illustrated in FIGS. 1 through 6, below.

FIG. 1 shows a view of an ultrasound transducer device 1 for continuous imaging as envisioned in the '845 patent. Transducer device 1 is adhered to the chest wall, between the ribs 23 of a patient. A conductor 2 is shown coming out of the top cover 10 of transducer device 1. Conductor 2 couples an ultrasound-activating signal from an ultrasound processor 50 to a transducer that is located within device 1 and positioned adjacent to the patient's body. Conductor 2 also couples, to ultrasound processor 50, an ultrasound echo signal reflected from tissue within the patient's body. The ultrasound echo signal is processed by ultrasound processor 50 to produce an image on display 60.

FIGS. 2 and 3 are, respectively, a perspective view of one embodiment of transducer device 1 and a partial, cross-section view of transducer device 1 mounted on a patient's body, taken along line 3—3 of FIG. 2. Transducer device 1 comprises a hollow enclosure 6 with an ultrasound transducer 16 mounted inside the bottom of enclosure 6. Conductor 2 is connected to transducer 16 and exits the assembly through a hole in the top cover 10. A holding pad 4 has a hole (not shown) in its center, a collar 8 attached to its top side around the hole and an adhesive layer 5 affixed to its underside. Enclosure 6 is held within collar 8. The top cover 10 includes a projecting stub 12, which is used for manually adjusting and rotating the transducer assembly in relation to holding pad 4. In use, transducer device 1 is adhered to the skin surface 21 of a patient.

FIG. 4 shows an embodiment of a transducer device 1a that permits remote orientation adjustment. FIGS. 5 and 6 show partial cross sectional views taken along line 5—5 of FIG. 4. Transducer device 1a is identical to transducer device 1 except for the addition of an adjusting assembly. All other parts of transducer device 1a are the same as those described for transducer device 1 and are identified in FIGS. 4, 5 and 6 with the same numerals as are used in FIGS. 2 and 3.

The adjusting assembly comprises an actuator support structure 22 and three actuating pins 24. FIG. 6 shows the result of an operator pushing down on one or two of the actuating pins 24. This action causes the enclosure 6 to swivel with one side downwards, placing the face of the transducer 16 at an angle to the patient's skin surface 21 and thereby adjusting the area scanned by transducer 16. Actuator pins 24 can be moved either manually or by a small remotely controlled mechanism (not shown) mounted on top of support structure 22. Such a remote controlled mechanism facilitates remote adjustment of the scanning area.

For many applications in medical ultrasound, especially vascular and cardiac applications, it is often desirable to selectively image tissues or blood. Contrast agents such as encapsulated air bubbles have been shown in the prior art to improve the visibility of these selected tissues. Additionally, such contrast agents have proven useful in the localized delivery of drugs.

U.S. Pat. No. 5,190,766 to Ishihara, entitled Method Of Controlling Drug Release By Resonant Sound wave, which is incorporated herein by reference, describes a method of using ultrasound for controlling the release of a drug from a drug carrier. The drug carrier is typically a suspension containing microcapsules. The fundamental principle behind this method is that when the drug carrier is insonified with a sound wave having a frequency corresponding to the resonance frequency of the drug carrier, the sound energy is absorbed and ruptures the microcapsules, allowing release of the drug. The drug can thus be selectively administered to a local region of a patient's body. Such isonification is performed using a standard transducer on a dosage by dosage basis. In other words, for each dose of the drug a separate ultrasound session has to be scheduled.

The present Inventor has recognized a need for an ultrasound system that provides continuous imaging of a patient in conjunction with the release of an agent from a carrier. Furthermore, such a system should measure a physiological parameter of the patient and automatically dispense the carrier into the patient's body on a continuous basis. Additionally, some form of monitoring should be performed to evaluate the effectiveness of the system.

The present Inventor has discovered that the ultrasound unit, described in the '845 patent, can be advantageously used in a system which continuously controls the release of a drug from a drug carrier that has been introduced into the patient's body. Further, such a system can continuously and automatically provide a localized delivery of agent, thereby substantially enhancing the usefulness of the system described in the '766 patent.

SUMMARY OF THE INVENTION

The present invention is an ultrasound system and method that enables release of an encapsulated agent from a carrier. The encapsulated agent can be a therapeutic agent, i.e., a drug, or it can be a contrast agent for improving the quality of an ultrasound image.

An ultrasound transducer is adhered to a patient's body over an organ of interest, and then adjusted for optimal ultrasound imaging. Once the transducer has been adjusted, it is locked into place so as to fix the imaging plane. An imaging technician is thus not required to maintain the desired plane. An ultrasound exposure can then continue unabated according to a predefined schedule. The ultrasound system can be programmed to produce emissions based on varying parameters such as drug type, carrier type, organ of interest, disease state, and patient state and condition.

In the preferred embodiment, the ultrasound system measures a physiological parameter of the patient to evaluate the patient's response to an agent. Thereafter, the system determines whether the dosage of the agent should be increased or decreased, and if so, it adjusts the quantity of the agent delivered by an injection, intravenous carrier, or other transport means.

The present invention offers several improvements over the prior art. The present invention allows for continuous drug delivery and response monitoring of a patient over a period of time without requiring the presence of a dedicated ultrasound technician. Advantageously, the invention can store sequential images over a period of time for subsequent review and trend analysis. It also enables medical personnel to visualize a region of interest in a patient, pre-drug, peri-drug, and post-drug release. In addition, it tracks the amounts of encapsulated agent and carrier delivered to the patient over time.

DETAILED DESCRIPTION OF THE PREFERRED EMBODIMENTS

Figure 1:
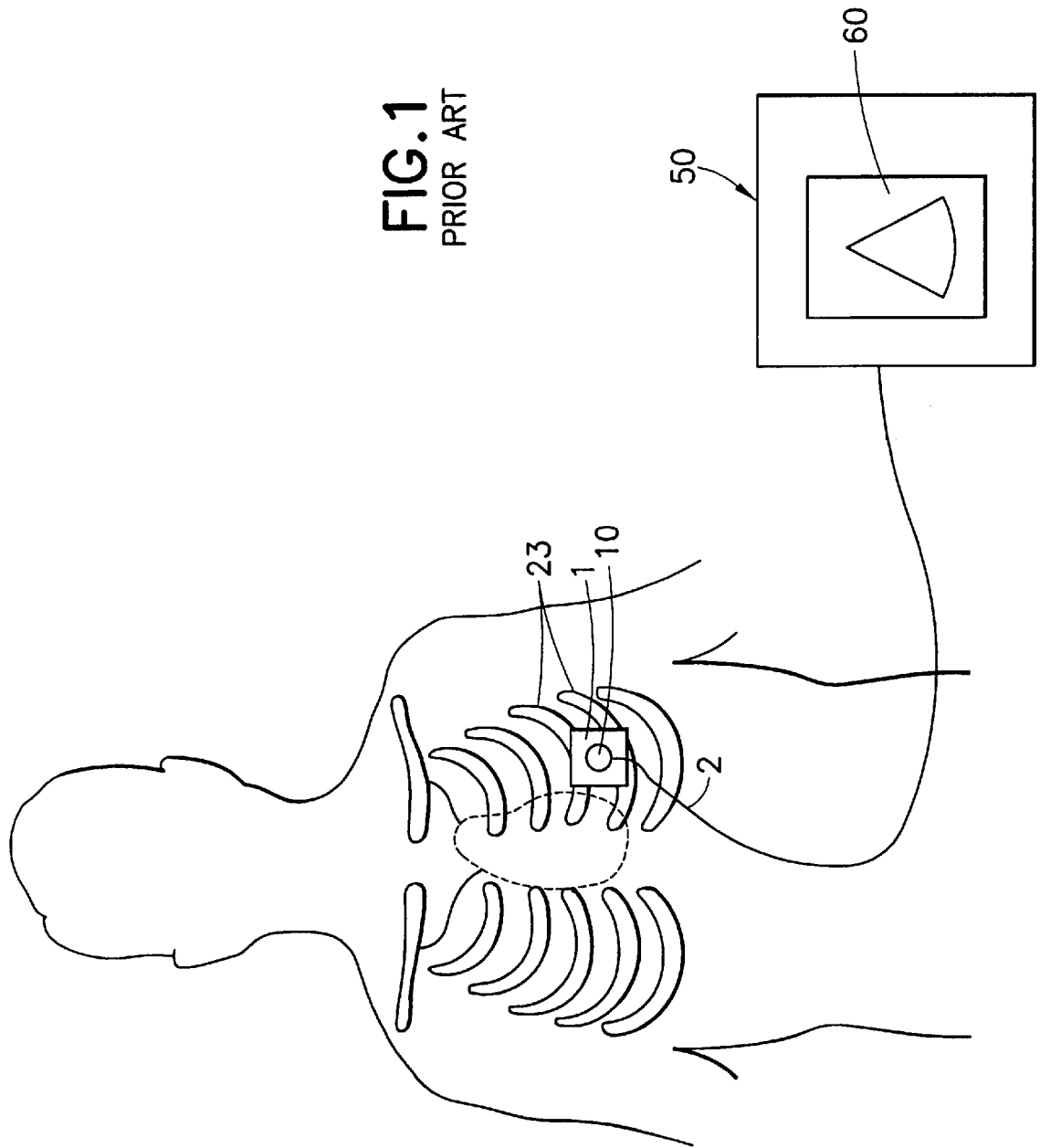
FIG. 1 is a view showing an ultrasound transducer device affixed on a patient's chest, particularly on his left side between the ribs for monitoring the heart according to the prior art.
Figure 2:
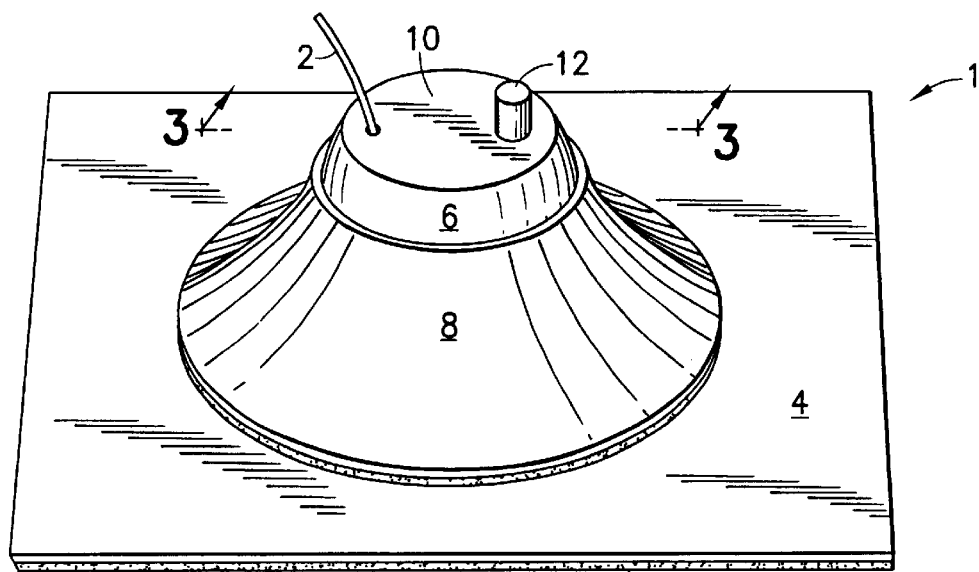
FIG. 2 is a perspective view of a prior art ultrasound transducer device for continuous imaging.
Figure 3:
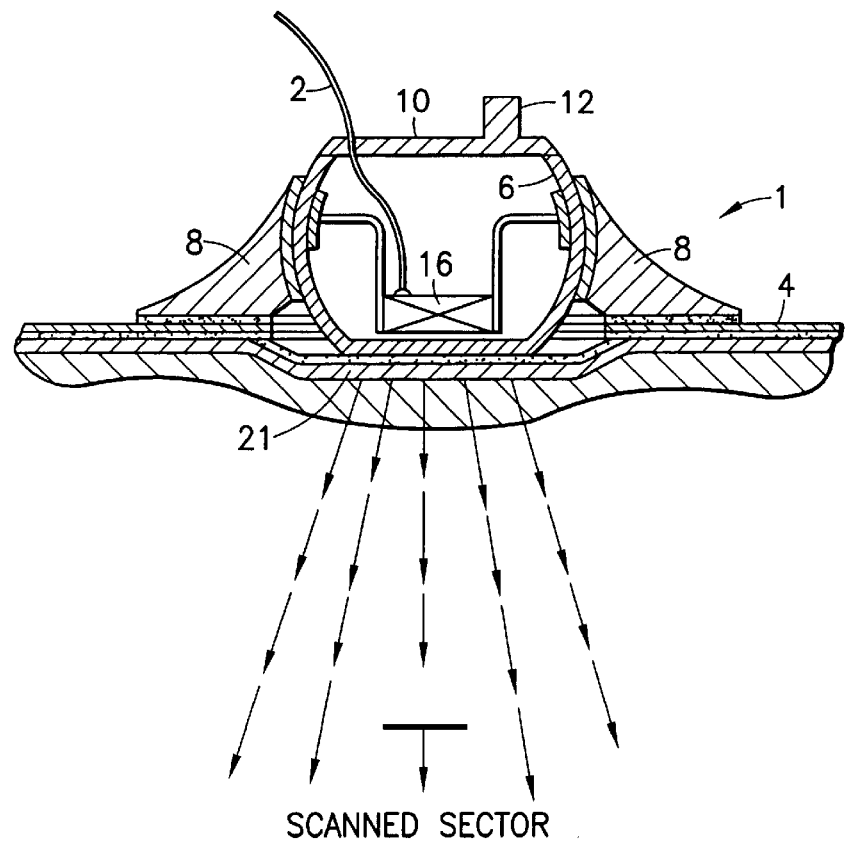
FIG. 3 is a partial cross-section view of a prior art ultrasound transducer device for continuous imaging taken alone line 3—3 of FIG. 2, particularly showing the device adhered to a patient's body and in place for projecting an ultrasound scanning beam.
Figure 4:
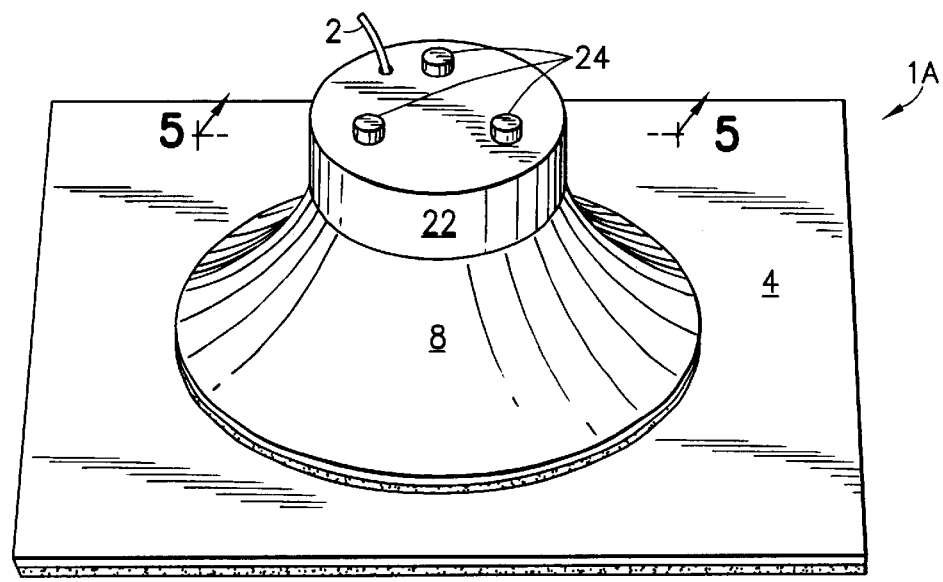
FIG. 4 is a perspective view of a second prior art ultrasound transducer device for continuous imaging.
Figure 5:
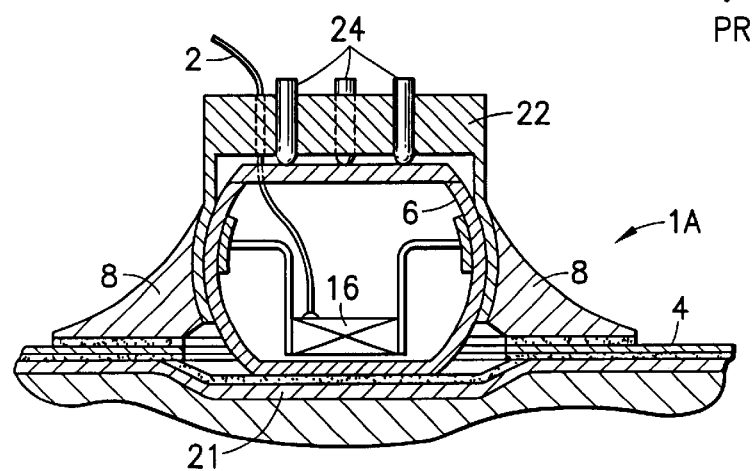
FIG. 5 is a partial cross-section view of the second prior art ultrasound transducer device taken along line 5—5 of FIG. 4, showing the device adhered to a patient's body.
Figure 6:
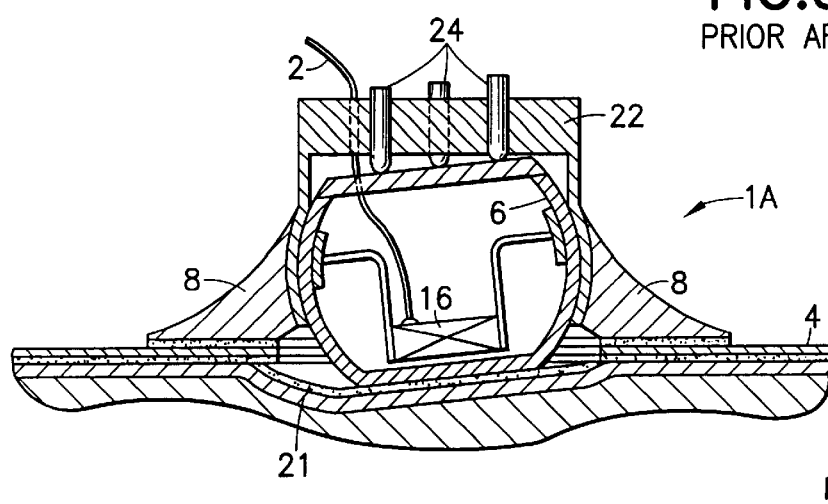
FIG. 6 is a partial cross-section view of the second prior art ultrasound transducer device taken along line 5—5 of FIG. 4, showing the device adhered to a patient's body, and useful in explaining the action of top actuating pins in tilting the ultrasound transducer to adjust the angle of the ultrasound beam.
Figure 7:
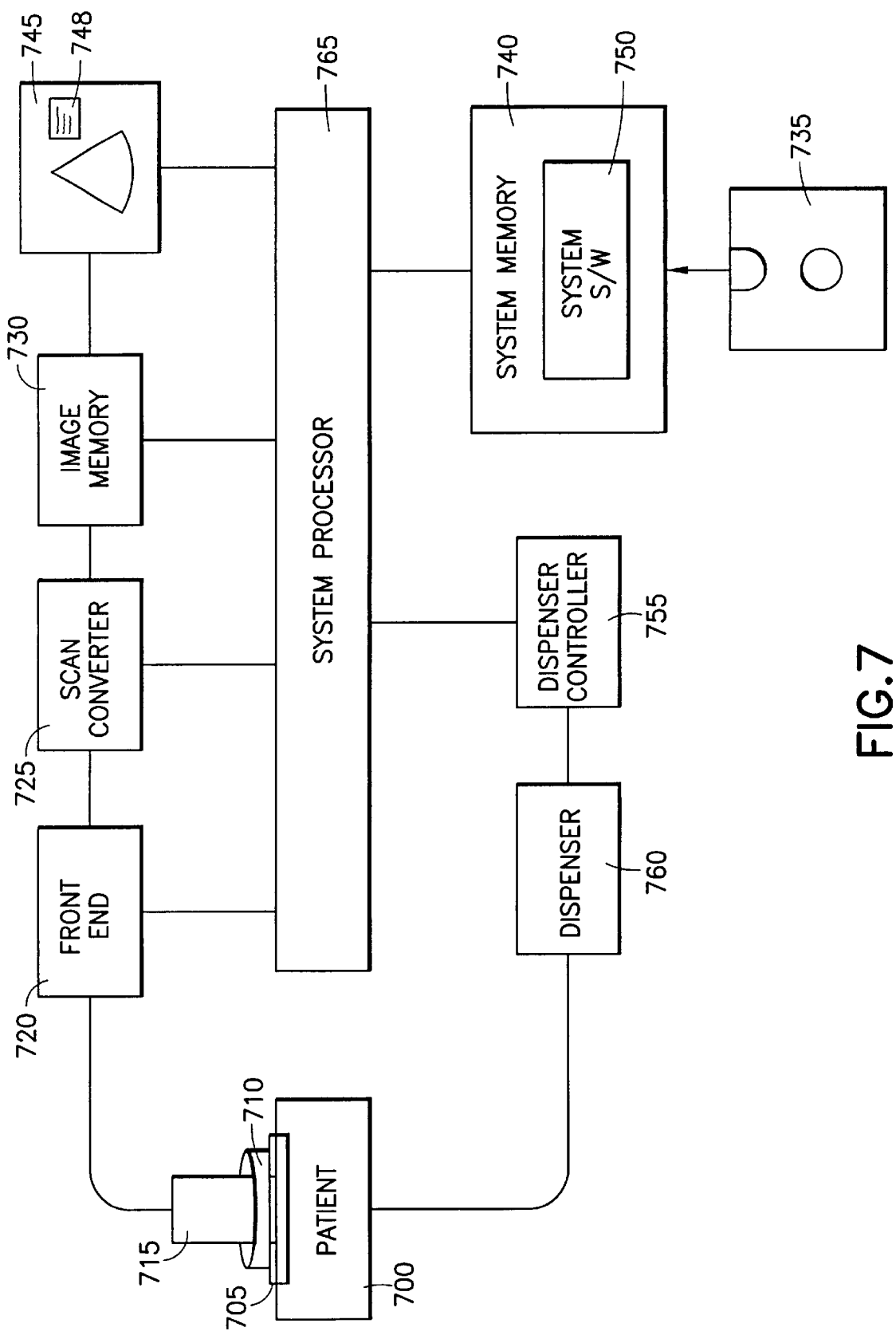
FIG. 7 is a block diagram of an ultrasound system according to the present invention.
Figure 8:
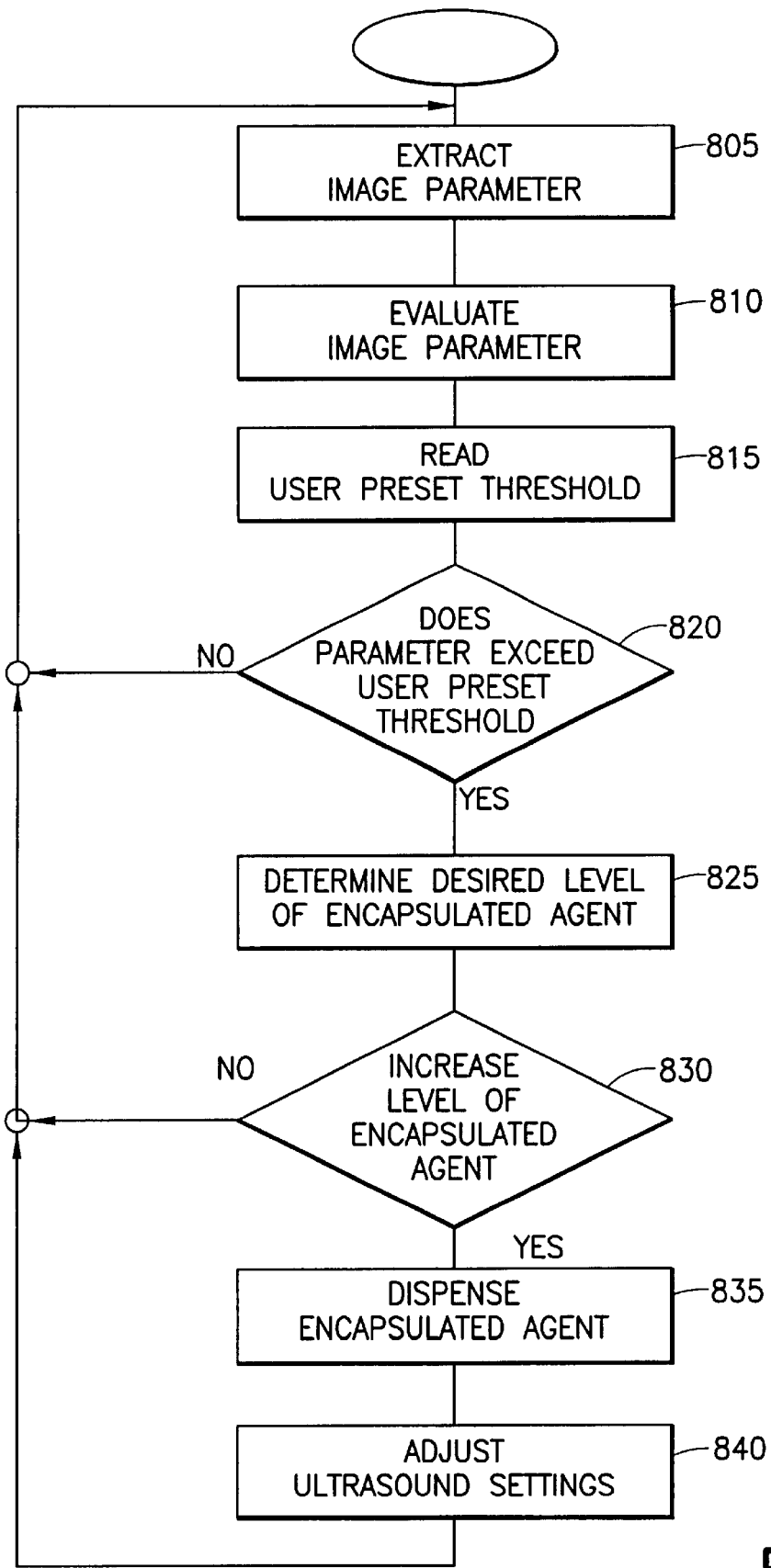
FIG. 8 is a flow chart of a process for controlling the release of an encapsulated agent from a carrier according to the present invention.

FIG. 7 is a block diagram of an ultrasound system according to the present invention. The system includes a transducer 715 connected to a front end 720. A system processor 765 interfaces with front end 720, a scan converter 725, an image memory 730, a display 745, a system memory 740 and a dispenser controller 755. System memory 740 includes system software 750. The system also includes a dispenser 760, which interfaces with dispenser controller 755.

Transducer 715 is mounted within a housing 710 that is secured by a means, such as an adhesive pad 705, to a patient 700. Transducer 715 is movable within housing 710 to allow for adjustment of the orientation of transducer 715 to obtain an optimal ultrasound-imaging plane. The adjustment can be made manually by a technician, or by a remotely controlled mechanism (not shown). After this adjustment, the technician need not continuously monitor the ultrasound system. This mounting arrangement permits continuous imaging of a region, i.e., a plane or volume, within patient 700.

Transducer 715 represents an ultrasonic transducer for transmitting and receiving an ultrasonic signal for generating an image of a scanned tissue in the body of patient 700. It also represents an ultrasonic transducer for transmitting an ultrasonic signal that causes the release of an agent from a carrier that has been introduced into the patient's body. Transducer 715 can be constructed as either a single transducer providing both functions, or as two independent transducers.

Transducer 715 uses piezoelectric elements typically arranged in an array, e.g., a one-dimensional phased array, a two-dimensional phased array, an annular array, a mechanical scanned element or a variation of such arrays. These piezoelectric arrays are well known in the industry. Operating frequencies will typically be in the range of 1.5 to 10 MHz. In the case of a two-dimensional phased array transducer, the imaging plane can be steered and focused electronically in both the lateral and elevational directions.

Front end 720 transmits ultrasonic signals to, and receives ultrasonic echo signals from, transducer 715. In a transmit mode it creates an ultrasonic beam scanning line using a waveform generator. It also generates an ultrasonic signal with sufficient magnitude to insonify the carrier and to cause the release of the agent from therein. The scanning and release functions may be provided by a single beam, or by two individual beams. Front end 720 controls signal parameters such as beam direction, magnitude, frequency, duration, and time of transmission.

In a receive mode, front end 720 receives and processes ultrasonic echo signals to produce a video signal representing tissue or another substance in the region being scanned in patient 700. The video signal is sent to scan converter 725.

Scan converter 725 correlates the video signal with the scanning line to produce an image signal that represents the region being scanned in patient 700. This image signal is sent to image memory 730.

Image memory 730 stores the image signal received from scan converter 725. As described below, the image signal will be used to create an image that will be presented on display 745. Also, the image signal can be further processed to distinguish features detected in the scanned region of patient 700. For example, multiple video frames can be displayed or evaluated to show a trend over a period of time.

Display 745 is a monitor for displaying the image represented by the image signal from image memory 730. Display 745 can be any conventional analog or digital display means including a cathode ray tube or a plasma panel display. In addition to displaying the image of the scanned region, display 745 displays supplementary data 748. Supplementary data 748 can summarize a physiological parameter of patient 700, or provide information regarding the carrier that has been dispensed or the agent that has been released.

Dispenser 760 represents a means for introducing the carrier into the body of patient 700, preferably an intravenous delivery system. However, the carrier can also be introduced by injection, absorption through the skin, ingestion or inhalation. Dispenser controller 755 controls the operation of dispenser 760. More particularly, it designates the quantity of, and the time at which, the carrier will be dispensed.

System processor 765 coordinates and controls the operation of the ultrasound system. The system can be programmed to produce ultrasound signals based on varying parameters such as drug type, carrier type, organ of interest, disease state, and patient state and condition. Additionally, system processor 765 processes video image data and other physiological data, such as EKG and respiration data that has been received from other equipment, to extract features of interest for further analysis. For example, linear and non-linear echoes can be distinguished for two-dimensional imaging and doppler imaging. Backscatter from a region of interest can also be evaluated to measure contrast agent concentration over a period of time (e.g., acoustic densitometry and acoustic quantification). This allows for the further evaluation of features such as local perfusion, regional perfusion, vessel diameter, tissue backscattered energy and blood velocity.

System processor 765 evaluates the image data to measure a physiological parameter of patient 700, e.g., heart rate, ejection fraction, cardiac output, left ventricular (LV) volume, and blood pressure feedback from a catheter or cuff. In response to this measurement, system processor 765 directs controller 755, to further control dispenser 760, for dispensing a quantity of the carrier at a particular time.

System processor 765 also calculates the quantity of the carrier and the agent released into the patient's body. Instantaneous and cumulative quantities can be calculated. The results of these calculations are indicated on display 745 as supplementary data 748.

System memory 740 contains programs and data, and in particular, system software 750, for execution by system processor 765. While the procedures required to execute the invention hereof are indicated as already loaded into system memory 740, they may be configured on a storage media, such as disk 735 for subsequent loading into system memory 740.

FIG. 8 is a flowchart of a process for controlling release of an encapsulated agent from a carrier according to the present invention. The process can be used with an ultrasound system capable of continuous imaging of a region, i.e., a plane or volume, inside a patient's body and controlling release of an agent from a carrier, such as the ultrasound system of the present invention, described above. The encapsulated agent can be a therapeutic agent, such as a drug, or it can be a contrast agent for improving the quality of an ultrasound image.

Generally, the process according to the present invention measures a physiological parameter of a patient and, based on that measurement, dispenses the carrier and subsequently controls the release of the agent from the carrier. The process begins with step 805.

In step 805, image data is examined and a physiological parameter is extracted. For example, the image data can be a series of images taken over a period of time and showing blood flow through the patient's heart. The process then advances to step 810.

In step 810, the physiological parameter is measured and evaluated. For example, the volume of blood flowing through the patient's heart can be quantified, and a rate of blood flow, that is, blood volume per unit of time, can be calculated. The process then advances to step 815.

In step 815, a physiological threshold value is obtained. The threshold value can be predetermined and read from a table, it can be set by the user, or it can be a dynamic value based on another measured or calculated parameter. As an example, the threshold value may indicate a specific rate of blood flowing through the heart. The process then advances to step 820.

In step 820, the measured physiological parameter is compared to the threshold value. The relational operator of the comparison, e.g., less than, equal to, or greater than, depends on the implementation and the nature of the physiological parameter that is being considered. For example, in one case, the comparison may determine whether the measured blood flow is greater than the threshold value, whereas in a second case the comparison may determine whether the measured blood flow is less than the threshold value. Generally, the comparison determines whether the measured physiological parameter is within a tolerable range of a target value. For the current illustration, if the measured physiological parameter does not exceed the threshold value, then the process loops back to step 805. If the measured physiological parameter does exceed the threshold value, then the process advances to step 825.

In step 825, the process determines a desired level of the agent based on the measured physiological parameter. For example, given a particular rate of blood flow, the process determines a desired level of the agent that should be administered to the patient. The process then advances to step 830.

In step 830, the process determines whether more of the agent should be administered to the patient. More particularly, the process determines whether the desired level, indicated from step 825, has been released into the patient. If the administered level of the agent does not need to be increased, then the process loops back to step 805. If the administered level of the agent does need to be increased, then the process advances to step 835.

In step 835, a quantity of the carrier is dispensed into the patients' body. The process then advances to step 840.

In step 840, an operating parameter of the ultrasound signal is adjusted based on the measured physiological parameter from step 810. The operating parameter can include beam direction, magnitude, frequency, duration, and time of transmission. Thereafter, the ultrasound signal insonifies a volume of the patient's body and thereby causes the release of the encapsulated agent from the carrier into the volume. The process then loops back to step 805.

The present invention offers several novel applications. First, it permits continuous or periodic release of an agent over a flexible configurable schedule, without requiring a dedicated ultrasound technician. Second, the system can be used therapeutically and delivery of the agent can be localized to a target site. For example, in chemotherapy a drug can be applied to a malignant tumor, potentially avoiding global side effects. Third, an organ's response to a drug can be evaluated by diagnostic imaging or monitoring subsequent to drug delivery. This can be particularly helpful where the invention is used to store sequential images over a period of time for subsequent review and trend analysis. Fourth, the invention can be configured to dispense and control the release of both a drug and a contrast agent in a consolidated program of drug treatment and response monitoring.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. An ultrasound system for imaging of a region inside a patient's body and for controlling release therein of an encapsulated agent from a carrier, said system comprising:
   a housing secured to said patient's body;
   a transducer mounted within said housing to enable continuous imaging of said region to measure a physiological parameter of the patient;
   means to evaluate the physiological parameter;
   means for controlling said transducer to insonify said region with an ultrasonic signal and to thereby cause release of said encapsulated agent from said carrier into said region in response to the evaluation of said physiological parameter; and
   means for processing an ultrasonic echo signal to produce an image of said region.

2. The ultrasound system recited in claim 1, further comprising further means for processing said ultrasonic echo signal to measure a physiological parameter of said patient.

3. The ultrasound system recited in claim 2, further comprising dispensing means for introducing said carrier into said patient's body, and wherein said further means controls operation of said dispensing means in accord with said measure of said physiological parameter.

4. The ultrasound system recited in claim 3, further comprising means for indicating to a user at least one of: a quantity of said carrier dispensed, a quantity of said encapsulated agent released into said patient's body, and said measured physiological parameter.

5. The ultrasound system recited in claim 2, wherein said means for controlling said transducer controls an operating parameter of said ultrasonic signal in dependence upon said measured physiological parameter.

6. The ultrasound system recited in claim 1, further comprising a means for moving said transducer within said housing.

7. The ultrasound system recited in claim 1, wherein said encapsulated agent is selected from the group consisting of: a drug, and a contrast agent.

8. A method for controlling release of an encapsulated agent from a carrier into a patient's body comprising the steps of:
   measuring a physiological parameter of a patient based on an ultrasonic echo signal; comparing said measured physiological parameter to a threshold; and
   transmitting an ultrasonic signal to insonify a region of said patient's body and thereby cause release of said encapsulated agent from said carrier into said region in accord with said measured physiological parameter.

9. The method recited in claim 8, further comprising repeating said steps of measuring, comparing, and transmitting.

10. The method recited in claim 8, further comprising:
    dispensing said carrier into said patient's body in accord with said measured physiological parameter.

11. The method recited in claim 10, further comprising indicating to a user at least one of: a quantity of said carrier dispensed, a quantity of said encapsulated agent released into said patient's body, and said measured physiological parameter.

12. The method recited in claim 8, further comprising setting an operating parameter of said ultrasonic signal in dependence upon said measured physiological parameter.

13. The method recited in claim 8, wherein said encapsulated agent is selected from the group consisting of: a drug, and a contrast agent.

14. A memory media that stores a program for controlling a processor for controlling release of an encapsulated agent from a carrier into a patient's body comprising:
    means for controlling said processor to measure a physiological parameter of a patient based on an ultrasonic echo signal;
    means for controlling said processor to compare said measured physiological parameter to a threshold; and
    means for controlling said processor to transmit an ultrasonic signal to insonify a region of said patient's body and thereby cause release of said encapsulated agent from said carrier into said region in accord with said measured physiological parameter.

15. The memory media recited in claim 14, further comprising means for controlling said processor to dispense said carrier into said patient's body in accord with said measured physiological parameter.

16. The memory media recited in claim 15, further comprising means for controlling said processor to indicate to a user at least one of: a quantity of said carrier dispensed, a quantity of said encapsulated agent released into said patient's body, and said measured physiological parameter.

17. The memory media recited in claim 14, further comprising means for controlling said processor to set an operating parameter of said ultrasonic signal in dependence upon said measured physiological parameter.

18. The memory media recited in claim 14, wherein said encapsulated agent is selected from the group consisting of: a drug, and a contrast agent.

19. An ultrasound system comprising:
    a transducer secured to a patient's body so as to enable continuous imaging of said region;
    a dispenser capable of introducing a carrier, encapsulating an agent, into the patient;
    a monitor outputting values indicative of a physiological parameter of the patient; and
    a control circuit responsive to the monitor that causes the dispenser to introduce the carrier into the patient and to adjust the transducer to cause the release of the agent.

20. An ultrasound system, as set forth in claim 19, wherein the monitor comprises software, executed by the control circuit, that evaluates images produced by the transducer to measure the physiological parameter.

* * * * *